United States Patent [19]

Weikel

[11] 4,360,126
[45] Nov. 23, 1982

[54] ROTARY DENTAL AMALGAM DISPENSER

[76] Inventor: Maurice M. Weikel, 3537 S. Buena Vista Dr., Las Vegas, Nev. 89121

[21] Appl. No.: 190,627

[22] Filed: Sep. 25, 1980

Related U.S. Application Data

[63] Continuation-in-part of Ser. No. 951,079, Oct. 13, 1978, abandoned.

[51] Int. Cl.³ .............................................. G01F 11/22
[52] U.S. Cl. ........................................ 221/96; 222/308
[58] Field of Search ................... 366/602; 221/96, 93; 222/362, 129.3, 136, 370, 129.4, 181, 308

[56] References Cited

U.S. PATENT DOCUMENTS 3,168,213  2/1965  DeGon ........................... 222/181 X
4,199,081  4/1980  Mason ............................ 222/181 X Primary Examiner—Stanley H. Tollberg
Attorney, Agent, or Firm—Fulwider, Patton, Rieber, Lee & Utecht

[57] ABSTRACT

A trigger actuated rotary dental amalgam dispenser is provided with a material distribution shell within which a transport carriage is rotated in a concave depression under the control of a trigger actuator. The shell is constructed with liquid conduit channels to carry mercury from a reservoir atop the shell to a measuring chamber in the carriage. Upon actuation of the trigger, a measuring chamber, otherwise held in communication with the mercury reservoir by a spring bias on the trigger, is rotated relative to the shell so that the mercury in the measuring chamber flows through an outlet channel in the shell and is discharged through a dispensing well. Concurrently, a slide with a silver receptacle tray is repositioned to receive another tablet of silver, and dispense this tablet into the dispensing well when the trigger is released and the biasing spring returns the slide to registration with the dispensing well. The volume of the measuring chamber is adjustable by means of a metering rod which can be advanced or retracted relative to the measuring chamber. Preferably a micropore filter is located in communication with the measuring chamber by means of a relief vent when the measuring chamber is in communication with the mercury reservoir. This allows air to escape as mercury fills the volume of the measuring chamber, yet the mercury cannot escape. Also, a vacuum break vent is preferably located to communicate with the measuring chamber when that chamber is in communication with the outlet channel.

23 Claims, 19 Drawing Figures

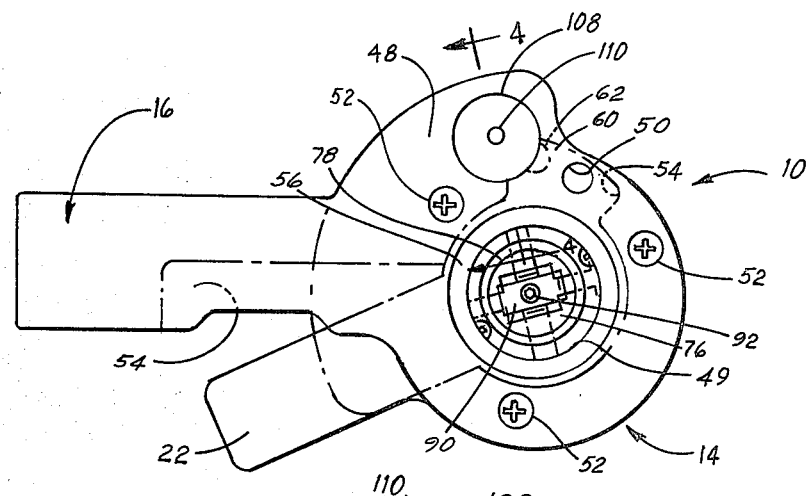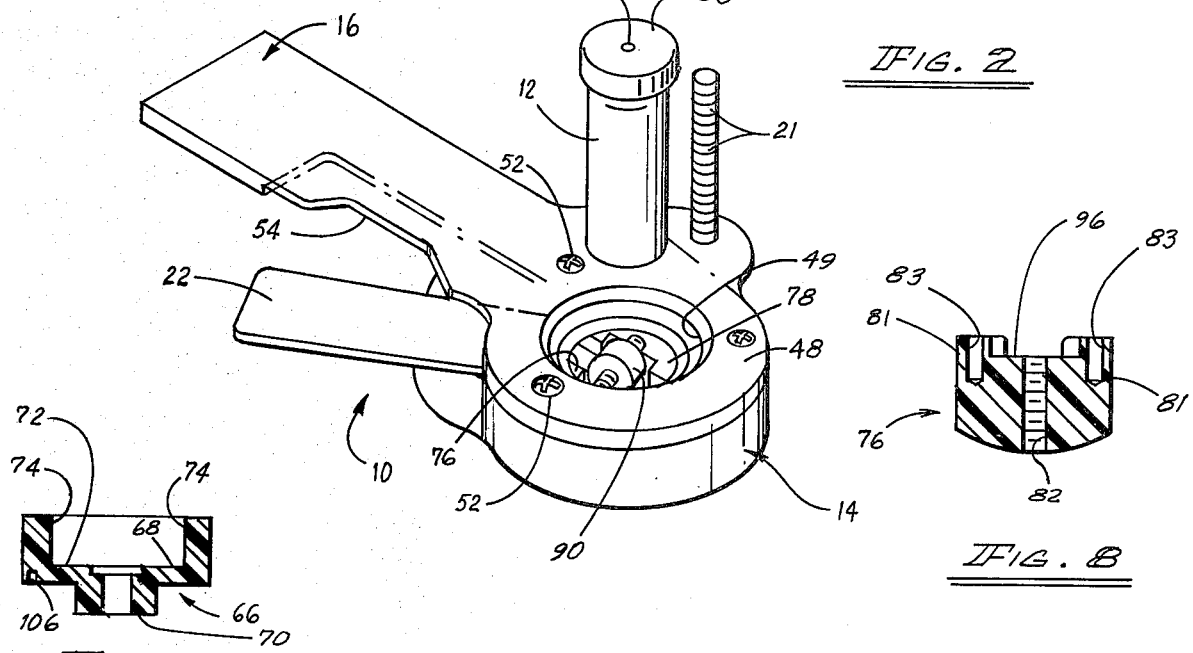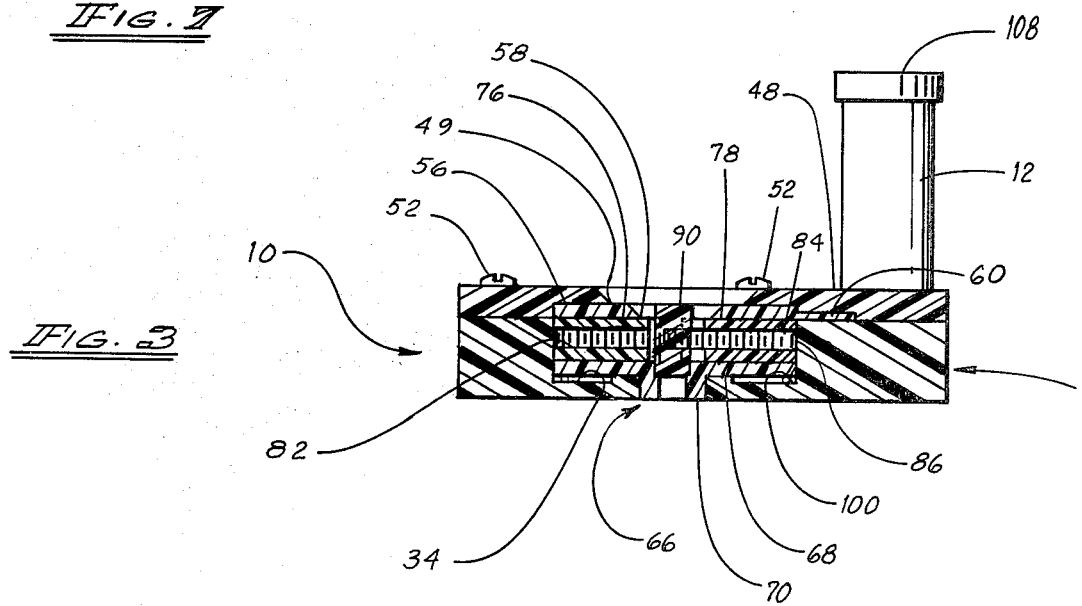

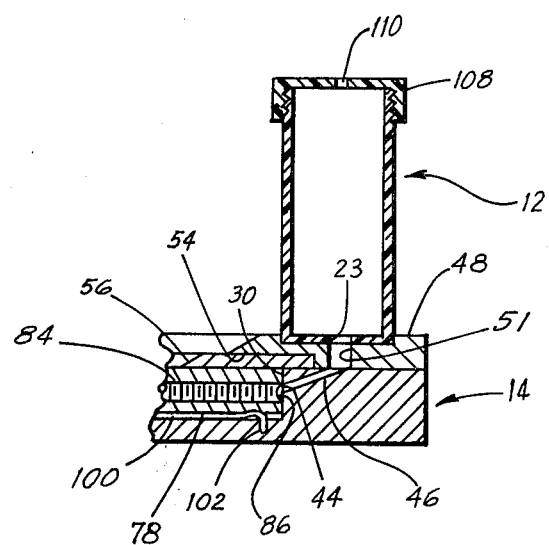
FIG. 4
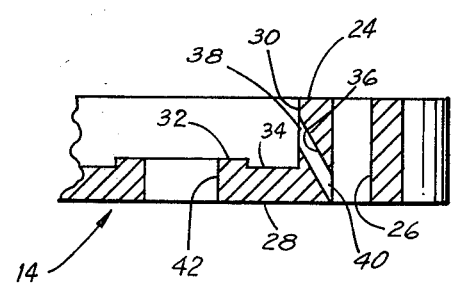
FIG. 5
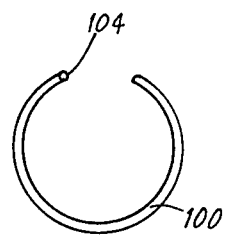
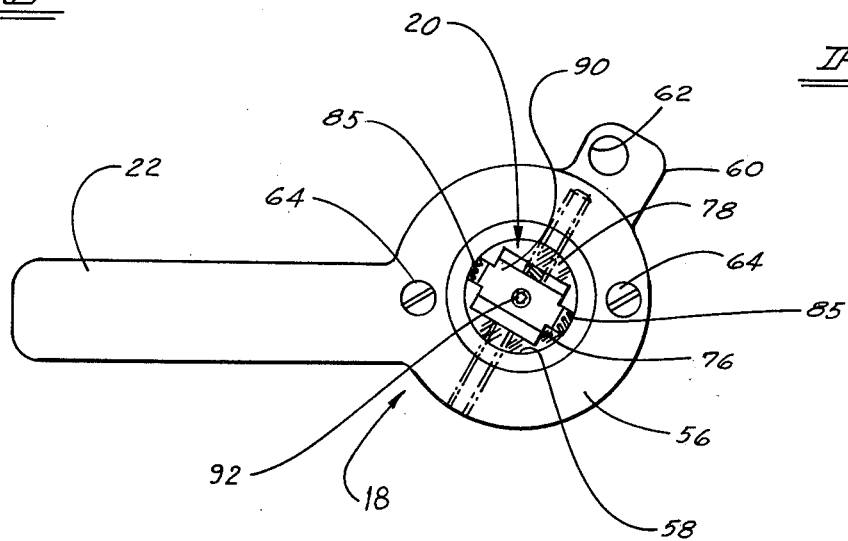
FIG. 6
FIG. 9

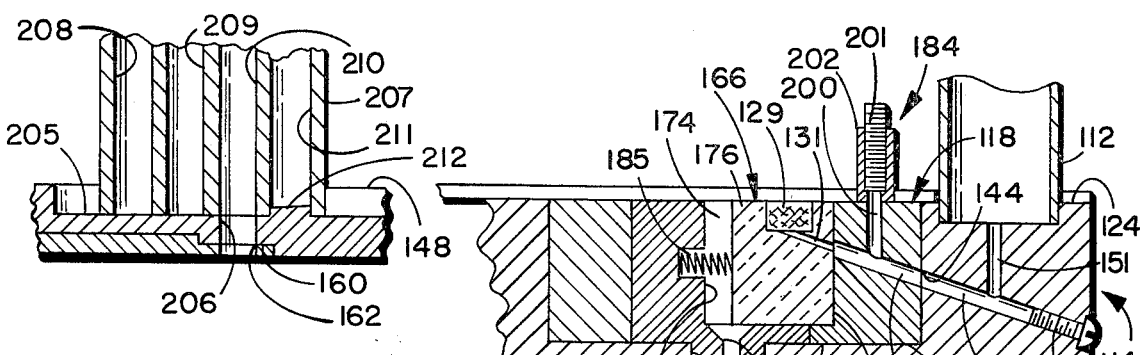
FIG. 13
FIG. 14
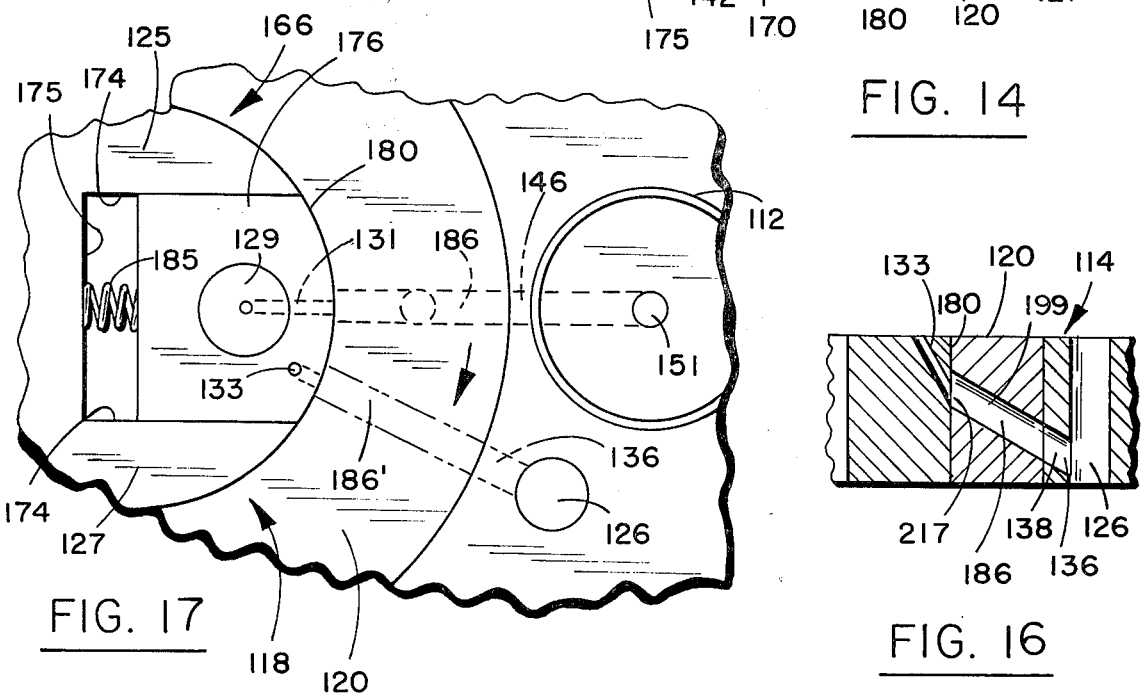
FIG. 17
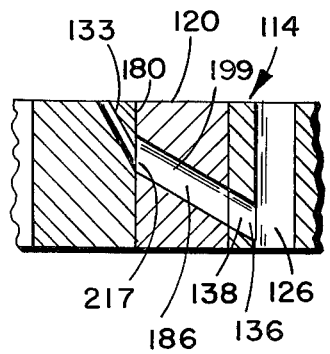
FIG. 16
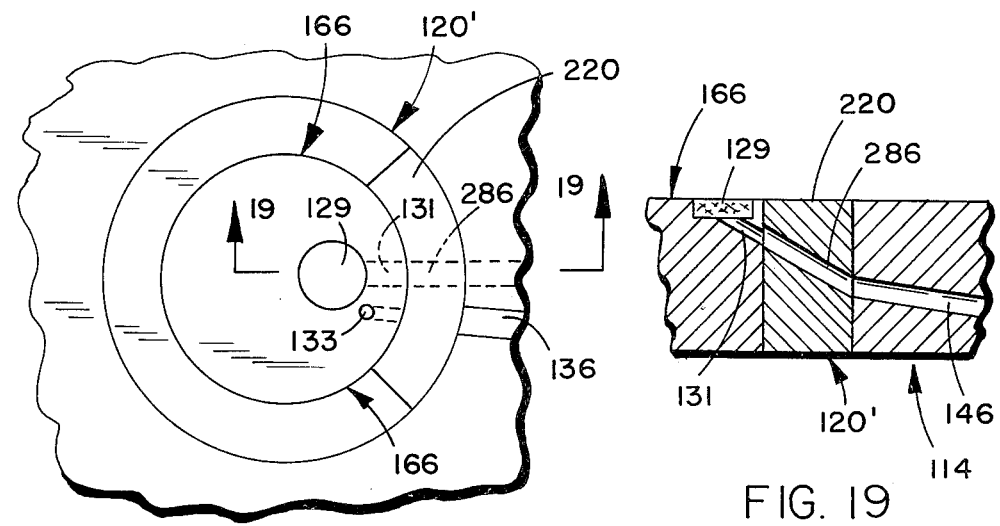
FIG. 18
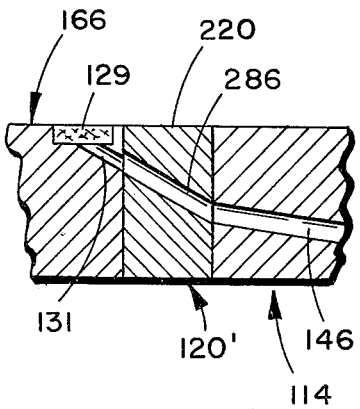
FIG. 19

ROTARY DENTAL AMALGAM DISPENSER

BACKGROUND OF THE INVENTION

This application is a continuation-in-part of U.S. Application Ser. No. 951,079, filed Oct. 13, 1978, and now abandoned.

FIELD OF THE INVENTION

The present invention relates to devices for dispensing mercury and silver for mixture into a dental amalgam.

DESCRIPTION OF THE PRIOR ART

In the past, various devices have been proposed to effectuate dispensation of aliquot quantities of mercury and silver for mixture to form a dental amalgam. The amalgam, forms a soft, pliable paste when the silver and mercury are initially mixed but quickly and permanently hardens to form a permanet filling for a tooth.

The various prior art devices employed for dispensing the amalgam components have been characterized as employing a reciprocal slide and a reservoir gating arrangement to allow silver and mercury to be dispensed. Such reciprocating mechanisms are subject to considerable wear because of the high degree of usage to which they are subjected and because of undesirable torsional forces which are applied to them. As a result, mercury leakage occurs and imprecise aliquots of mercury are dispensed with conventional reciprocating dispenser mechanisms.

SUMMARY OF THE INVENTION

The present invention involves the use of a rotatable transport carriage that is actuated by a trigger to rotate within a surrounding shell to effectuate dispensation of aliquot quantities of silver and mercury for mixing to form a dental amalgam. The shell includes a handle and an upper surface upon which the mercury reservoir and a stack of pressed powdered silver tablets are located. Within the shell there is an aperture to accept the tablets of silver from the stack, one at a time. Also within the shell, a channel leads from the mercury reservoir to an inlet port interface with a rotatable transport carriage. Within the transport carriage a measuring chamber is defined which can be moved into communication with the inlet port. Alternatively, when the transport carriage is rotated, the measuring chamber is rotatable to an outlet port interface with the shell. This outlet port leads to a downwardly inclined channel which empties into a dispensing well.

Rotation of the transport carriage also carries a slide having a tray therein. A single tablet of silver is captured within the tray at any one time and is also carried to the dispensing well upon release of the trigger mechanism. The trigger is spring biased so that when released, the hub and slide will return to a predetermined static position in which the tray is in vertical registration with the dispensing well.

Preferably, the volume of the measuring chamber is adjustable. Adjustment is performed by means of a metering rod. The rod is longitudinally adjustable in an attitude of advancement toward or withdrawal from the measuring chamber. This decreases or increases the volume of the chamber, and hence decreases or increases the volume of mercury transported within the chamber from the inlet port to the outlet port. The transport carriage moves in sliding sealed engagement with the shell, so that mercury is trapped in the chamber and is carried from the inlet to the outlet port without leakage.

In order to allow the measuring chamber to completely fill, the channel from the mercury reservoir is preferably constructed with a vertical duct extending downwardly from the mercury reservoir, and an inclined duct extending upwardly toward the measuring chamber. The measuring chamber itself is inclined with its lower extremity at the level of the outlet port. A central stationary hub may be employed and a micropore filter may be located in the hub. A relief vent may be defined within the hub for communication with the measuring chamber when the transport carriage is rotated to a position at which the measuring chamber is also in communication with the channel to the mercury reservoir. The mercury reservoir is located above the measuring chamber so that the existance of a head of mercury forces mercury from the lower extremity of the vertical duct beneath the reservoir up the inclined duct of the channel and into the measuring chamber. The measuring chamber fills completely, since displaced air is forced out of the dental amalgam dispenser through the relief vent and through the micropore filter. The micropore filter will not, however, allow mercury to escape.

Preferably also, a vacuum break vent is defined in the stationary central hub for communication with the measuring chamber when the measuring chamber is rotated into alignment with the outlet port. This ensures that all of the mercury empties from the measuring chamber into the dispensing well, and that a vacuum does not form which might retain mercury in the measuring chamber.

The dental amalgam dispenser is preferably adapted to receive a tablet dispensing cartridge having a plurality of parallel, equally spaced vertical tubes for holding columnar stacks of tablets of silver. A desired tube may be positioned in a track directly above the aperture in the shell, so that tablets of silver may be dispensed from the selected tube, one at a time. When all of the tablets have been dispensed from one tube, the cartridge is advanced incrementally along the track to bring another tube into alignment with the aperture.

It is an object of the present invention to provide a dental amalgam dispenser with a spring loaded trigger mechanism that can be operated to effectuate rotary motion of a transport carriage to discharge aliquot quantities of mercury and silver for mixture into an amalgam. In this connection, it is a further object to avoid the undesirable wear attributable to the application of unwanted torque in reciprocal amalgam dispensing devices.

The invention may be described with greater clarity and particularly by reference to the accompanying drawings.

DESCRIPTION OF THE DRAWINGS

FIG. 1 is a plan view of one embodiment of a dental amalgam dispenser according to the invention.

FIG. 2 is a perspective view of the embodiment of FIG. 1.

FIG. 3 is a sectional elevational view of the dispenser of FIG. 1 with the hub at an intermediate position of rotation.

FIG. 4 is a sectional elevational detail taken along the lines 4—4 of FIG. 1.

FIG. 5 is a sectional elevational detail of the shell of FIG. 1 in isolation taken through the dispensing well.

FIG. 6 is a plan view of the dispenser transport carriage and trigger of FIG. 1 in isolation from the shell.

FIG. 7 is an elevational sectional view of a carriage hub baseplate used in the embodiment of FIG. 1 viewed in isolation.

FIG. 8 is a plan section of a slab used in the hub construction of the embodiment of FIG. 1.

FIG. 9 is a plan isolation view of a spring for biasing the hub of the embodiment of FIG. 1.

FIG. 13 is a sectional elevational detail taken along the lines 13—13 of FIG. 11.

FIG. 14 is a sectional elevational detail taken along the lines 14—14 of FIG. 12.

FIG. 16 is a sectional elevational detail taken along the lines 16—16 of FIG. 12.

FIG. 17 is a top plan detail of a portion of the embodiment of FIG. 10.

FIG. 18 is a top plan detail of a modified transport carriage in the embodiment of FIG. 10.

FIG. 19 is a sectional detail taken along the lines 19—19 of FIG. 18.

DESCRIPTION OF THE EMBODIMENT

Figure 11:
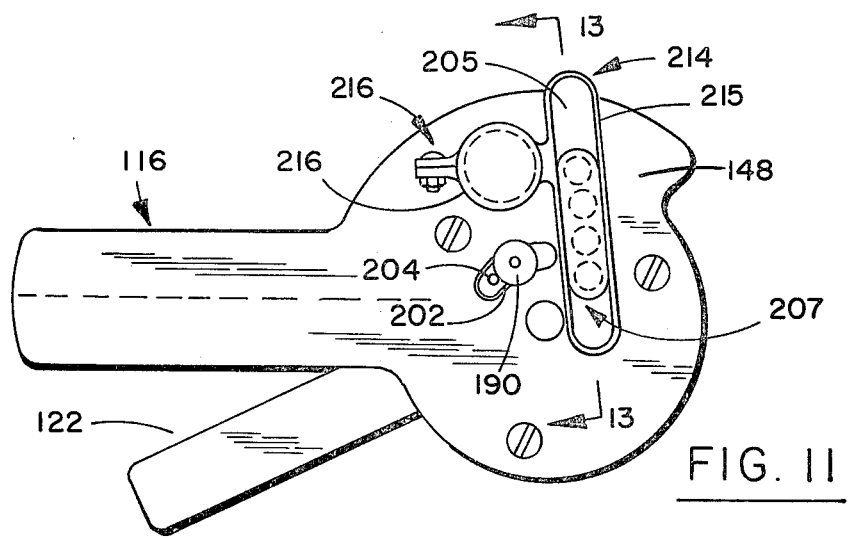
FIG. 11 is a top plan view of the embodiment of FIG. 10 of the invention.

One embodiment of the invention is depicted in FIGS. 1-6. With reference to FIG. 2, a dental amalgam dispenser 10 is depicted having a hollow cylindrical tank or reservoir bottle 12 for holding a supply of mercury and a stack of tablets 21 formed of silver, both positioned atop a cast solid plastic material distribution shell 14. The stack of tablets 21 may be laterally confined by any conventional means, such as within a transparent, hollow, cylindrical plastic tube. The material distribution shell 14 is a flat, squat, generally bell-shaped structure to which an elongated plastic handle 16 with a hand grip is rigidly attached. A large, central concave depression is defined in the material distribution shell 14 to receive a hub 20 of a transport carriage 18, depicted in isolation in FIG. 6. The generally disk shaped hub 20 is rotatably mounted in the central depression of the material distribution shell 14 and an elongated trigger mechanism 22 is rigidly attached to the hub 20.

The material distribution shell 14 is preferably a solid block of cast Lucite. The shell 14 is partially depicted in isolation in FIG. 5 and has flat parallel upper and lower surfaces 24 and 28 respectively with an irregular outer perimeter generally semicircular on one side and fan shaped on the other. A cylindrical bore extends vertically through the shell 14 between the flat upper and lower surfaces 24 and 28 to define a dispensing well 26. Roughly at the center of the shell 14, there is defined a concave depression or cavity having a vertical wall 30 extending in a circular configuration and having a floor with a raised coaxial pedestal 32 at the center surrounded by a recessed annular channel 34. The center of the concave depression defined by the wall 30 includes a vertical mounting aperture 42 in the middle of the pedestal 32. The mounting aperture 42 is useful in centering the hub 20 which fits into the concave depression in the shell 14. The dispensing well 26 is laterally displaced from the depression defined by the circular wall 30. A channel 36 of circular cross section slopes downwardly from a transfer outlet port 38 in the wall 30 to intersect the dispensing well 26 in a corresponding discharge port 40, as depicted in FIG. 5.

A transfer inlet port 44, circumferentially displaced from the transfer outlet 38 is defined in the wall 30 in shell 14 as depicted in FIG. 4. The transfer inlet port 44 is at the lower extremity of a downwardly sloping channel 46 which leads from the flat upper surface 24 within the structure of the shell 14. The channel 46 serves as a mercury conduit from the reservoir bottle 12. The inlet transfer port 44 is located in the wall 30 at a level slightly above the level of the transfer outlet port 38.

A Lucite handle 16, depicted in FIGS. 1 and 2, is rigidly secured to the shell 14. The handle 16 includes an elongated grip and terminates at one end in a configured mounting ring 48 having a large central positioning aperture 49 defined therein, and having a smaller tablet receiving aperture 50 radially displaced from the larger central positioning aperture 49. The aperture 50 is circumferentially displaced from vertical alignment with the dispensing well 26 in the shell 14 along an arc centered at the vertical axis of the hub 20. The handle 16 is fastened to the material distribution shell 14 by means of countersunken machine screws 52 spaced about the mounting ring 48. The mounting ring 48 also includes a vertical duct 51, located directly beneath the mercury reservoir bottle 12, depicted in FIG. 4.

A portion of the underside of the handle 16 is molded with an overhang on the upper surface to define a recess therebeneath, so that a gap exists between the structure of the handle 16 and the structure of the material distribution shell 14 in a patterned area denoted at 54 in FIGS. 1, 2 and 4. This area 54 corresponds to the shape of the area of movement of the trigger 22 directly beneath the handle 16 so that the trigger 22 is able to nest therewithin. The area 54 includes an elongated recess extending radially outward from the central aperture 49 in the mounting ring 48, an annular recess adjacent to the central aperture 49 radially interiorally from the screws 52 at the underside of the structure of the mounting ring 48, as indicated in FIG. 4, and also a recess radially displaced therefrom and extending between the dispensing well 26 and the aperture 50. By providing a gap between the structure of the handle 16 and the structure of the material transport shell 14, the elongated trigger 22 is accessible for grasping, and is easily rotatable toward the handle 16 and seats in the recess formed in the elongated portion of the recessed area 54 beneath the handle 16.

While one end of the elongated Lucite trigger 22 is accessible for manual manipulation, the opposite end of the trigger terminates in an annular mounting plate 56, visible in FIG. 6, which is received in the recessed area 54 between the material transport shell 14 and the mounting ring 48. The mounting plate 56 also includes a central access aperture 58 defined therein and a transversely extending sliding tab 60 with an aperture 62 therein. The aperture 62 serves as a tray to receive the disk shaped tablets 21 of silver and to carry them to the dispensing well 26, one at a time. The aperture 50 in the mounting ring 48, the aperture 62 in the tab 60 of the mounting plate 56, and the dispensing well 26 in the shell 14 are all of the same diameter and are spaced at the same radial distance from the axis of rotation of the hub 20 at the center of the depression bounded by the wall 30 in the material distribution shell 14. The aperture 62 in the tab 60 can be moved from either a position of alignment with the dispensing well 26, or to a position aligned with the aperture 50 in the mounting ring 48 when the trigger 22 is squeezed into the recess at the underside of the handle 16.

Countersunken machine screws 64 spaced diametrically opposite each other, as indicated in FIG. 6, attach the hub 20 to the underside of the mounting plate 56. The hub 20 includes a baseplate 66 which has vertical threaded apertures in upstanding portions thereof. The trigger 22 and the hub 20 are thereby rigidly rotatable together about the center of the depression formed in the material distribution shell 14. Together the trigger 22, including the mounting plate 56, and the hub 20 form the transport carriage 18 which is used to effectuate movement of mercury from the tank 12 and tablets 21 of silver, one by one, from the aperture 50, to the dispensing well 26.

The baseplate 66 has a generally disk shaped floor 68 having an annular boss 70 depending from its lower surface at its center, as depicted in FIG. 7. The boss 70 rotates within the aperture 42 in the shell 14 to center the baseplate 66 in the concave depression in the mounting shell 14, as indicated in FIG. 3. The baseplate 66 is not a completely solid structure, but rather has a very large expansive channel 72 defined therein. The channel 72 is bound by chordal walls 74 spaced equally from the axial center of the boss 70.

A pair of opposing radially projecting slabs 76 and 78, depicted in FIG. 6, are positioned in back to back relationship and are reciprocally movable within the channel 72 in the baseplate 66. The slab configuration is depicted in FIG. 8. The slabs 76 and 78 each are flat with straight vertical side walls 81, an outer curved surface 80, and an inner surface indented with a horizontally extending generally circular radially outwardly directed depression at 96. The side walls 81 of the slabs 76 and 78 reside in sliding contact with the chordal walls 74 of the baseplate 66. The slab 76 is depicted in isolation in a plan cross section in FIG. 8. The slabs 76 and 78 are of identical outer geometric configuration. The curved arcuate outer surfaces 80 conform to the curvature of the wall 30 of the depression in the material transport shell 14. Defined longitudinally through the centers of the slabs 76 and 78 are interiorally threaded radial bores 82 designed to receive an externally threaded rod 84, depicted in FIGS. 3 and 4. The slabs 76 and 78 differ from each other only in that the slab 76 has defined therein a pair of spring wells 83 parallel to the vertical walls 81 and parallel to the threaded bore 82. The wells 83 are adapted to receive and seat coil springs 85, visible in FIG. 6, which are maintained in compression between the slabs 76 and 78. The springs 85 bear against the inner surface of the slab 78 and bais the slabs 76 and 78 radially outward from the center of the mounting hub 20.

The outer radial extremity of the metering rod 84 terminates in a concave configuration which forms an axially outwardly opening cup, visible in FIG. 4. The convex surface 80 of slab 78 slides in sealed engagement with the wall 30. A measuring chamber 86 is defined between the concave extremity of the metering rod 84 and the wall 30, as depicted in FIGS. 3 and 4. Near the center of the metering rod 84, there is an annular adjustment spool 90 having an axial bore to receive the metering rod 84 and a smaller threaded radial bore adapted to receive an allen head set screw 92, visible in FIGS. 1 and 6. The adjustment spool 90 is thereby rotatable in a plane perpendicular to the plane of rotation of the hub 86. Rotation of the adjustment spool 90 in a vertical plane in one direction advances the metering rod 84 radially outward within the tapped bore 82 to reduce the volume in the measuring chamber 66. Rotation of the adjustment spool 90 in the opposite direction withdraws the metering rod 84 inward toward the center of the hub 20 to increase the volume of the measuring chamber 86. Adjustment of the position of the spool 90 is thereby used to adjust the volume of mercury transported within the measuring chamber 86. The adjustment spool 90 moves transversely with the advancement or withdrawal of the metering rod 84, since the radial depressions 96 in the slabs 76 and 78 are formed deep enough to accomodate such lateral movement.

A torsion spring 100 is depicted in isolation in FIG. 9. The spring 100 includes a downwardly turned fastening stub 102 which is received within a corresponding well in the floor of the depression in the material distribution shell 14, as depicted in FIG. 4. At the opposite end of the arcuate spring 100, there is an upturned anchoring stub 104, which is received in a corresponding cavity 106 in the baseplate 66 depicted in FIG. 7. The spring 100 thereby holds the entire carriage 18 in a predetermined position of rotation relative to the handle 16 and material distribution shell 14. Squeezing the trigger 22 toward the handle 16 tightens the spring 100. When the trigger 22 is released, the spring 100 returns the carriage 18 to its normal rest position depicted in FIG. 1. In this position, the transfer inlet port 44 is in communication with the measuring chamber 86 formed between the metering rod 84 and the wall 30.

The reservoir bottle 12 has a flat bottom with an aperture 23 therein. The reservoir bottle 12 is normally capped with a threadably engaged plastic cap 108 having a breather hole 110 defined therein to form a vacuum break. When the trigger 22 and the handle 16 are released, as in FIG. 1, mercury from the reservoir bottle 12 travels through the central aperture 23 therein and through the aligned aperture 51 in the mounting ring 48 to the downwardly sloping channel 46 in the material distribution shell 14. From the channel 46, mercury enters the measuring chamber 86 at the upper extremity thereof through the inlet transfer port 44. Since the volume of the measuring cavity 86 has been predetermined by positioning of the adjustment spool 90, only a prescribed volume of mercury enters the chamber 86.

In the operation of the invention, a quantity of mercury is initially transferred from the mercury reservoir 12 to the measuring chamber 86. When the trigger 22 is squeezed into the recess formed in the underside of the handle 16, the hub 20 is rotated and the cavity 86 leaves communication with the inlet port 44. As the hub 66 rotates, the mercury is entrapped within the cavity 86 by the close fit of the arcuate surface 80 of the slab 78 against the wall 30. The surface 80 moves in sliding sealed engagement with the wall 30 to prevent leakage of the mercury from the cavity 86. Such an intermediate position of transfer is depicted in FIG. 3.

When the trigger 22 has been brought to an extreme position of movement in which it abuts the extremity of the recess in the underside of the handle 16, the measuring chamber 86 in the hub 20 is aligned with the outlet port 38 in the material distribution shell 14. Since the transfer outlet port 38 leads to a downwardly inclined channel 36, the entire quantity of mercury within the cavity 86 flows through the channel 36 to the intersection with the dispensing well 26 at port 40, depicted in FIG. 5. The mercury then falls into a mixing container below, (not depicted).

Concurrently with movement of the hub 20 when the trigger 22 is squeezed into its extreme position at the underside of the handle 16, the tray 62 formed in the radial tab 60 in the mounting plate 56 is brought into registration with the tablet receiving aperture 50 in the mounting ring 48. Since the stack of silver tablets 21 are positioned directly above the tablet receiving aperture 50, the lowermost tablet 21 drops downward into the tray 62. Upon release of the trigger 22, the spring 100 carries the hub 20 in counter-rotation to return the tray 62 to alignment with the dispensing well 26. When the hub 66 has completed this counter-rotation, the tablet 21, theretofore entrapped in the tray 62, falls through the dispensing well 26 and into the mixing container beneath. The dental amalgam dispenser 10 thereby is able to effectively and consistently dispense aliquot quantities of mercury and silver for mixing to form a dental amalgam. When the trigger 22 is released also the spring 100 returns the measuring chamber 86 to communication with the inlet transfer port 44 and the tray 62 to alignment with the dispensing well 26. The trigger 22 can be operated any number of times to replicate the quantities of silver and mercury dispensed. Each operation of the trigger 22 will be accompanied by dispensation of a quantity of mercury from the measuring cavity 86 followed by dispensation of a tablet 21 of silver from the tray 62.

Figure 12:
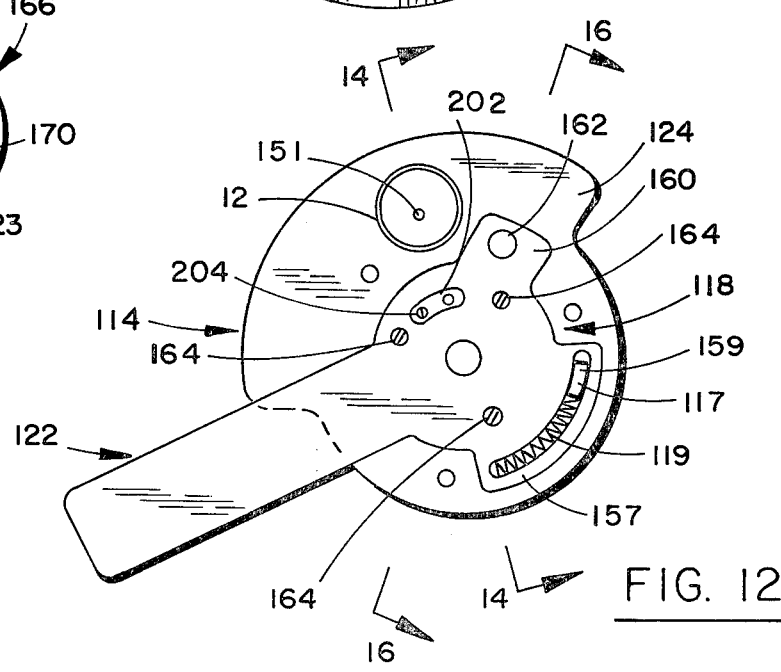
FIG. 12 is a top plan view in isolation of the material distribution shell and the transport carriage of the embodiment of FIG. 10.

A preferred embodiment of the invention is illustrated in FIGS. 10–17, which depicts a dental amalgam dispenser 111. The dental amalgam dispenser 111 is similar in a number of respects to the dental amalgam dispenser 10 depicted in FIGS. 1–9. The dental amalgam dispenser 111 has a material distribution shell 114 which has a flat upper surface 124, depicted in FIGS. 12 and 14. An arcuate cavity 117 depicted in FIG. 12 is defined in the flat upper surface 124 of the material distribution shell 114. A coil spring 119 is positioned in the arcuate cavity 117. A cylindrical plastic mercury reservoir 112 rests in a circular concavity in the flat upper surface 124 of the shell 114 near the periphery thereof. An inlet channel is defined in the shell 114 in the form of a vertical duct 151 which descends from the mercury reservoir 112, as illustrated in FIG. 14, and an inclined duct 146 which intersects both the vertical duct 151 and a transfer inlet port 144 at the upper and interior extremity of the duct 146. The duct 146 is drilled through the wall of the material distribution shell 114 for ease of machining, and the outer and lower extremity of the duct 146 is closed with a blocking screw 121.

The material distribution shell 114 also has a vertical bore therethrough defining a dispensing well 126, as illustrated in FIG. 16. A transfer outlet port 138 is located at the upper extremity of a downwardly and outwardly inclined channel 136 which leads from the central depression to the vertical dispensing well 126 in the material distribution shell 114.

Figure 15:
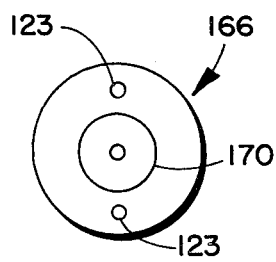
FIG. 15 is a bottom view in isolation of the hub of the dental amalgam dispenser of FIG. 10.

The material distribution shell 114 has a central depression or recess defined therein and a stationary hub 66, depicted in FIG. 15, is secured to the material distribution shell 114 by machine screws which are directed upwardly through the floor of the shell 114 on either side of the center thereof and into threaded vertical apertures 123 in the hub 66. The hub 66 also has a depending boss 170 which extends through an aperture 142 in the floor of the shell 114, as illustrated in FIG. 14.

The disposition of the hub 166 is illustrated in FIG. 17 and is formed with side partitions 125 and 127 which have arcuate outer walls and parallel cordal inner wall, 174. The cordal inner walls 174 terminate against a transverse back wall 175. The walls 174 and 175 define a radial cavity within the hub 166. A slab 176 is located within the radial cavity and is flat with straight vertical side walls that move in sliding engagement with the walls 174 of the side partitions 125 and 127. The slab 176 also has an outer curved surface 180. The slab 176 is forced radially outwardly from the back wall 176 by a coiled spring 185 which is compressed between the slab 176 and the back wall 175.

A shallow, vertical well is defined within the slab 176 and a disk-shaped micropore filter 129 is positioned therewithin, as depicted in FIGS. 14 and 17. A relief vent 131 is defined within the slab 176 of the hub 166 and slopes from the micropore filter 129 at an angle downwardly to the arcuately curved wall 180. A vacuum break vent 133 extends from the flat top surface of the slab 176 downwardly and outwardly at an angle also to intersect the arcuately curved wall 180.

The dental amalgam dispenser 111 also includes a transport carriage 118 which includes an annular, cylindrical ring 120 and a trigger 122 attached thereto. The annular ring 120 has a lower lip 137 which is entrapped between the hub 166 and the floor of the material distribution shell 114.

In the embodiment of FIGS. 10–17, the transport carriage 118 is constructed entirely of plastic and the ring 120 is rotatable in sliding sealed engagement with the hub 166 and with the interior cylindrical wall of the material distribution shell 114. The transport carriage 118 includes a measuring chamber 186 in the ring 120 which is defined as an inclined bore sloping inwardly from the material distribution shell 114 toward the hub 166, as depicted in FIG. 14. The lower extremity 199 of the measuring chamber 186 is at the vertical level of both the transfer outlet port 138, depicted in FIG. 16, and the transfer inlet port 144, depicted in FIG. 14.

As illustrated in FIGS. 16 and 17, a vacuum break vent 133 is defined in the annular ring 120 of the transport carriage 118. The vent 133 slopes at an angle downwardly to intersect the upper end 217 of the measuring chamber 186 when the measuring chamber 186 lies in communication with the transfer outlet port 136. Mercury in the measuring chamber 186 thereupon falls freely through the lowermost end 199 of the measuring chamber 186 into the dispensing well 126 when the measuring chamber 186 is positioned in communication therewith.

Figure 10:
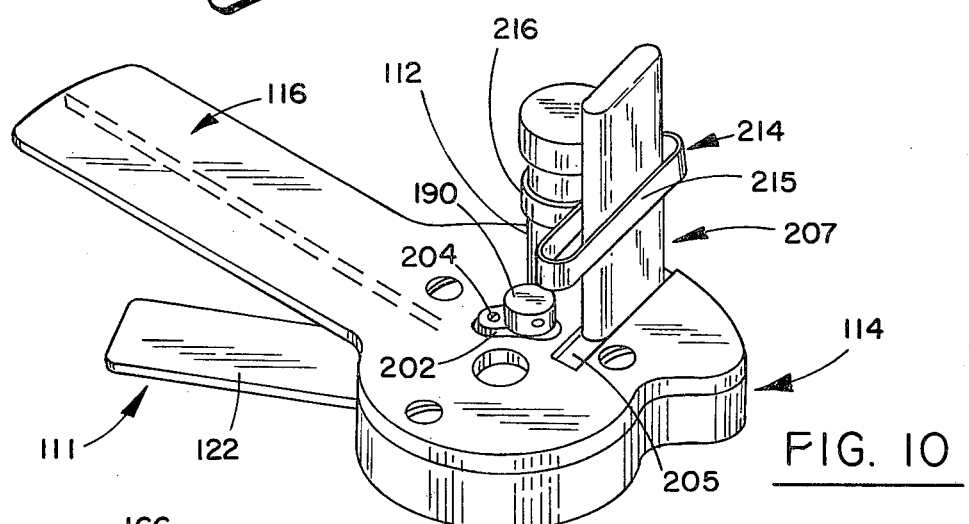
FIG. 10 is a perspective view of a preferred embodiment of a dental amalgam dispenser according to the invention.

A vertical bore is defined downwardly from the upper surface of the annular ring 120 in the transport carriage 118 to receive the lower, unthreaded extremity 200 of a threaded metering rod 184. The upper threaded portion 201 of the metering rod 184 is threadably engaged in a short, arcuate, plastic mounting block 202. The mounting block 202 is secured by a screw 204 to a mounting plate 156 of the trigger 122, as depicted in FIGS. 10–12. A thumbwheel adjusting knob 190, fastened by an allen head set screw to the metering rod 184 is used to advance and retract the metering rod 184 to increase and decrease the volume of the measuring chamber 186.

The mounting plate 156 of the trigger 122 is fastened to the annular ring 120 of the transport carriage 118 by means of machine screws 164, as depicted in FIG. 12. The mounting plate 156 has an outwardly directed flange 157 with a finger 159 depending downwardly therefrom. The finger 159 depends into the arcuate cavity 117 of the material distribution shell 114. The coil spring 119 is thereby maintained in compression in the cavity 117 to bear against the finger 159. This biases the trigger 122 in a counterclockwise direction relative to the material distribution shell 114, as viewed in FIG. 12.

The mounting plate 156 also has a slide 160. The slide 160 is similar in configuration and operation to the radial tab 60 in the mounting plate 56 of the embodiment of FIGS. 1-9. The slide 160 has defined therein an aperture 162. The aperture 162 in the slide 160 serve as a tray to receive the tablets of silver and to carry them to the dispensing well 126, one at a time, in a manner hereinafter to be described.

Atop the material distribution block 114 there is an injection molded plastic handle 116, depicted in FIGS. 10 and 12. The handle 116 includes an elongated grip and terminates at one end in a configured mounting deck 148. The mounting deck 148 is similar in many respects to the mounting ring 48 of the embodiment of FIGS. 1-9, but also includes a track 205 illustrated in FIGS. 10, 11 and 13. The track 205 in the mounting deck 148 has an aperture 206 defined therein above the slide 160. The track 205 is formed as a channel in the upper surface of the mounting deck 148 and is adapted to receive a tablet dispensing cartridge 207.

The tablet dispensing cartridge 207 is an oblong, thin, upright plastic structure into which a plurality of parallel, equally spaced vertical tubes 208-211 of equal diameter are defined for holding columnar stacks of tablets of silver, such as the tablets 21 illustrated in FIG. 2.

The cartridge 207 is moveable along the track 205 to align a selected one of the tubes 208-211 with the aperture 206 in the mounting deck 148 to dispense tablets from the selected tube through the aperture 206 and into the slide 160. In the channel of the track 205 there is a positioning lug 212, which is a short pedestal configured to project upwardly from the track 205 and to slope upwardly away from the aperture 206. The positioning lug 212 fits into one of the tubes 208-211, or into abutment with the wall defined at one of the ends of the cartridge 207 to position the next adjacent one of the tubes 208-211 directly into vertical alignment with the aperture 206 in the mounting deck 148. The engagement of the projecting lug 212 in an appropriate one of the tubes, or against the end of the cartridge 207, can be sensed by the user as the user moves the cartridge 207 along the track 205 so that proper vertical alignment of the selected one of the tubes 208-211 can be assured.

As illustrated in FIGS. 10 and 11, the dental amalgam dispenser 111 may be provided with a retaining bracket 214 which is configured with an oblong elongated band 215 to receive the cartridge 207 for longitudinal reciprocation therewithin. Attached to the band 215 is a mounting ring 216 which is of cylindrical annular configuration and is secured about the structure of the reservoir 112 by means of a locking screw and nut assembly 216, as illustrated in FIG. 11. When the locking assembly 216 is tightened, the retaining bracket 214 is secured relative to the material distribution shell 114 above the mounting deck 148. The cartridge 207 can thereby be adjustably positioned along the track 205 to align the selected tube 208-211 with the aperture 206 in the mounting deck 148, in the manner previously described. With the retaining bracket 214, the dental amalgam dispenser 111 can be moved freely about and the cartridge 207 will not fall out but will remain in position on the mounting deck 148.

In the operation of the dental amalgam dispenser 111, the cartridge 207 is first positioned in the track 205 and held within the confines of the retaining loop 215 of the retaining bracket 214. The cartridge 207 is longitudinally adjusted, using the positioning lug 212 in the manner described in connection with FIG. 13. The trigger 122 is then squeezed toward the handle 116. Sufficient force is required to compress the spring 119, depicted in FIG. 12, which otherwise biases the trigger 122 and handle 116 apart.

Before the trigger 122 and handle 116 are compressed, mercury flows from the reservoir 112 down the vertical duct 151 and up into the inclined duct 146, through the inlet port 144 and into the inclined measuring chamber 186, all illustrated in FIG. 14. Mercury will not pass through the micropore filter 129, but air displaced from the ducts 151 and 146 and the measuring chamber 186 is exhausted through the micropore filter 129. The head of mercury in the reservoir 112 is sufficient to force the mercury up the inclined duct 146 and the inclined measuring chamber 186. As previously noted, the adjusting knob 190 can be used to alter the amount of mercury in the measuring chamber 186.

When the trigger 122 and handle 116 are squeezed together, the annular transport carriage 118 rotates clockwise, as viewed in FIG. 17. The measuring chamber 186 moves in a clockwise direction to the position 186'. In this position the lower extremity 199 of the measuring chamber 186 is brought into communication with the outlet port 136, as illustrated in FIG. 16. Mercury thereupon flows out of the outlet port 136 from the measuring chamber 186 and into the dispensing well 126. The vacuum break vent 133 allows air to follow the mercury and enter the measuring chamber 186 so that droplets of mercury are not held back by a vacuum as might otherwise occur. Accordingly, the entire aliquot of mercury is discharged into the dispensing well 126.

As the handle 116 and trigger 122 are squeezed together, the aperture 162 in the slide 160 is brought into registration with the aperture 206 in the track 205 in the mounting deck 148. The lowermost tablet is dispensed from the cartridge 207 into the slide 160. When the trigger 122 is released, the spring 119 rotates the slide 160 counterclockwise, as viewed in FIG. 12, until the aperture 162 resides in vertical registration with the dispensing well 126. The tablet of silver discharged from the cartridge 207 into the slide 160 is thereby carried to the dispensing well 126.

A further modification of the invention is illustrated in FIGS. 18 and 19. In this modification the transport carriage 118' is constructed of a plastic ring 120' having a vertical, cylindrical wall with a gap therein. A metal insert 220 of arcuate configuration is positioned in this gap. A measuring chamber 286 is defined in the metal insert 220. By using a stainless steel insert 220, closer adherence to tolerances in the dimensioning of the measuring chamber 286 are possible. A central, stationary hub 166, with a micropore filter 129, relief vent 131, and vacuum break 133 are defined as previously described.

While several embodiments of the invention have been depicted, it should be understood that numerous other variations and modifications of the invention will undoubtedly become readily apparent to those familiar with dental amalgam dispensers. Accordingly, the invention should not be considered as limited to the specific implementations depicted and described, but rather is defined in the claims appended hereto.

I claim:

1. A dental amalgam dispenser comprising:
   a mercury reservoir
   a material distribution shell having a dispensing well extending from the upper to the lower surface thereof, a channel for conducting mercury from said mercury reservoir to a transfer inlet in an arcuate wall, and a channel for conducting mercury from a transfer outlet to said dispensing well, wherein said transfer outlet is located in said wall and is arcuately displaced from and vertically no higher than the level of said transfer inlet,
   a transport carriage coupled to said shell for rotation relative thereto about a vertical axis and including a tablet tray for carrying silver tablets to said dispensing well for discharge therein and wherein there is defined a measuring chamber, and said carriage is rotatable in sliding sealed engagement with said wall to a position in which said measuring chamber is in communication with said transfer inlet and alternatively to a position in which said measuring chamber is in communication with said transfer outlet.

2. The dental amalgam dispenser of claim 1 further comprising a handle connected to one of said shell and said carriage and a trigger connected to the other thereof, and spring means biasing said handle and trigger apart, whereby squeezing said handle and said trigger together brings said measuring chamber from communication with said transfer inlet to communication with said transfer outlet.

3. The dental amalgam dispenser of claim 1 wherein said carriage is equipped with means for varying the volume of said measuring chamber.

4. The dental amalgam dispenser of claim 1 further characterized in that said transport carriage is provided with a hub having an arcuate surface which moves in sealing engagement with said wall and wherein said measuring chamber is defined, and a slide is coupled to said hub for rotatable movement therewith and said slide contains said silver tablet tray.

5. The dental amalgam dispenser according to claim 1 further characterized in that said channel is defined in said material distribution shell as a vertical duct descending from said mercury reservoir and an inclined duct intersecting both said vertical duct and said transfer inlet, and further characterized in that said material distribution shell has a central recess defined therein, and a stationary hub is located at the center of said recess, and said transport carriage includes an annular ring rotatable in sliding sealed engagement with said hub within said recess in said material distribution shell.

6. The dental amalgam dispenser according to claim 5 further comprising a micropore filter located in said hub, and a relief vent is defined in said hub to extend between said micropore filter and said annular ring of said transport carriage and in communication with said measuring chamber when said carriage is rotated to said position in which said measuring chamber is in communication with said transfer inlet.

7. The dental amalgam dispenser according to claim 6 further characterized in that a vacuum break vent is defined in said hub to communicate with said measuring chamber when said carriage is rotated to said position in which said measuring chamber is in communication with said transfer outlet.

8. The dental amalgam dispenser according to claim 6 further characterized in that said measuring chamber is defined in said annular ring as an inclined bore sloping upwardly from said material distribution shell toward said hub.

9. The dental amalgam dispenser according to claim 8 further comprising a metering rod threadably engaged with said transport carriage for protrusion into said inclined bore to an adjustable extent, thereby providing means for altering the volume of said measuring chamber.

10. The dental amalgam dispenser according to claim 5 further characterized in that said hub is formed with a radial cavity therein, with a slab slidingly reciprocal in radial fashion within said radial cavity, and with a spring biasing said slab radially outward.

11. The dental amalgam dispenser according to claim 5 further characterized in that said annular ring of said transport carriage is constructed of plastic having a vertical, cylindrical wall with a gap therein, and a metal insert of arcuate configuration is positioned in said gap, and said measuring chamber is defined in said metal insert.

12. A dental amalgam dispenser comprising:
    a material distribution shell having a flat upper surface and within said shell there are defined
    (a) a dispensing well extending through said distribution shell from said flat upper surface to an outlet beneath,
    (b) a concave depression with a wall of circular cross section defined in said flat upper surface.
    (c) a channel from said flat upper surface to a transfer inlet in said wall,
    (d) a transfer outlet in said wall circumferentially displaced from said transfer inlet and no higher than the level thereof,
    (e) a downwardly inclined channel extending from said transfer outlet to said dispensing well,
    a transport carriage having a portion rotatable within said concave depression and in sliding sealing engagement therewith and containing a measuring chamber at the level of said transfer inlet, and with its lower extremity at the level of said transfer outlet,
    a mercury reservoir extending above said flat upper surface of said shell and in communication with said channel leading to said transfer inlet,
    slide means coupled for rotation with said carriage for receiving a measured quantity of silver from above said flat upper surface of said material distribution shell and for carrying it for discharge into said dispensing well.

13. A dental amalgam dispenser according to claim 12 further comprising adjustable metering means for altering the volume of said measuring chamber.

14. A dental amalgam dispenser according to claim 13 further characterized in that said transport carriage has a hub formed as a disk rotatable about its center and having a channel defined therein by vertical chordal walls equally spaced from the center of the disk, and a pair of opposing slabs are positioned in back to back relationship reciprocally movable within said channel, each of said slabs having arcuate outer surfaces which conform to said wall of said depression, and wherein said measuring chamber is defined within the outer surface of one of said slabs, and further comprising spring biasing means biasing said slabs outwardly from the center of said disk, and said adjusting means includes a radial rod extending within at least one of said slabs to said measuring chamber and adjustable lengthwise to vary the volume of said measuring chamber.

15. A dental amalgam dispenser according to claim 14 further characterized in that said radial rod is threadably engaged within said slab and further comprising an adjustment means fixedly secured to said rod and rotatable between said slabs in a plane perpendicular to the plane of rotation of said hub to selectively advance and withdraw said threaded rod relative to said chamber.

16. A dental amalgam dispenser according to claim 12 further comprising spring biasing means for biasing said transport carriage in rotation to bring said measuring chamber into communication with said channel leading to said transfer inlet.

17. A dental amalgam dispenser according to claim 16 further characterized in that an arcuate cavity is defined in said flat upper surface of said material distribution shell, and said spring biasing means is a coil spring positioned in said arcuate cavity, and further comprising a handle connected to said shell and said carriage includes a trigger having a finger that depends into said arcuate cavity, whereby said coil spring is maintained in compression in said cavity to bear against said finger, thereby biasing said trigger and said handle apart.

18. A dental amalgam dispenser according to claim 12 further comprising a micropore filter and a relief vent leading to said micropore filter and in communication with said measuring chamber when said measuring chamber lies in communication with said transfer inlet.

19. A dental amalgam dispenser according to claim 12 further comprising a vacuum break vent in communication with said measuring chamber when said measuring chamber lies in communication with said transfer outlet.

20. A dental amalgam dispenser according to claim 12 further comprising a mounting deck secured to said material distribution shell above said slide means and having a track with an aperture defined therein above said slide, and a tablet dispensing cartridge with a plurality of parallel, equally spaced vertical tubes of equal diameter for holding columnar stacks of tablets of silver is disposed in said track, whereby said cartridge is movable along said track to align a selected one of said tubes with said aperture to disperse tablets from said selected tube through said aperture into said slide.

21. A dental amalgam dispenser according to claim 20 further characterized in that said track includes a positioning lug to ensure alignment of said selected tube with said aperture.

22. A dental amalgam dispenser according to claim 21 further characterized in that said positioning lug fits into said tubes and is configured to project upwardly from said track and to slope upwardly away from said aperture.

23. A dental amalgam dispenser according to claim 20 further comprising a retaining bracket secured relative to said material distribution shell above said mounting deck and having an elongated opening therein to receive said dispensing cartridge for reciprocal movement therewithin.

* * * * *